(12) United States Patent
Chayen (10) Patent No.: US 7,214,266 B2
(45) Date of Patent: May 8, 2007

(54) METHODS OF CRYSTAL OPTIMIZATION

(75) Inventor: Naomi E. Chayen, London (GB)

(73) Assignee: Imperial Innovations Limited, London (GB)

( * ) Notice: Subject to any disclaimer, the term of this patent is extended or adjusted under 35 U.S.C. 154(b) by 501 days.

(21) Appl. No.: 10/680,390

(22) Filed: Oct. 2, 2003

(65) Prior Publication Data
US 2004/0106776 A1   Jun. 3, 2004

Related U.S. Application Data

(63) Continuation of application No. PCT/GB02/01559, filed on Apr. 2, 2002.

(30) Foreign Application Priority Data

Apr. 3, 2001   (GB) .................................. 0108287.4

(51) Int. Cl.
*C30B 1/06* (2006.01)
(52) U.S. Cl. ....................... 117/4; 117/2; 117/3; 117/11
(58) Field of Classification Search .................... 117/2, 117/3, 4, 11
See application file for complete search history.

(56) References Cited

U.S. PATENT DOCUMENTS

| 4,052,320 A | 10/1977 | Jakubowicz |
| 5,705,628 A | 1/1998 | Hawkins |

FOREIGN PATENT DOCUMENTS

| WO | WO 99/15876 | 4/1999 |
| WO | WO 01/30499 A1 | 5/2001 |
| WO | WO 01/92293 | 12/2001 |

OTHER PUBLICATIONS

Abbott, Alison, NATURE, *Structures by Numbers*, vol. 408, Nov. 9, 2000, pp. 130-132.
Abola et al, Nature Structural Biology, *Automation of X-ray Crystallography*, vol. 7, Nov. 2000, pp. 973-977.
Barrett et al, CELL, *Crystal Structure of a G:T/U Mismatch-Specific DNA Glycosylase: Mismatch Recognition by Complementary-Strand Interactions*, vol. 92, Jan. 9, 1998, pp. 117-129.
Blow et al, Protein Science, *Control of Nucleation of Protein Crystals*, vol.3, (1994), pp. 1638-1643.
Chayen, J. Appl. Cryst., *An Automated System for Micro-Batch Protein Crystallization and Screening*, vol. 23, (1990), pp. 297-302.
Chayen, J. Appl. Cryst., *A Novel Technique to Control the Rate of Vapour Diffusion, Giving Larger Protein Crystals*, vol. 30, (1997), pp. 198-202.
Chayen et al, Journal of Crystal Growth, *Microbatch Crystallization Under Oil—A New Technique Allowing Many Small-Volume Crystallization Trials*, vol. 122, (1992), pp. 176-180.

(Continued)

*Primary Examiner*—Felisa Hiteshew
(74) *Attorney, Agent, or Firm*—Nikolai & Mersereau, P.A.; C. G. Mersereau (57) ABSTRACT

The present invention provides an automated method of optimising crystallisation conditions for macromolecules comprising forming a trial comprising a sample comprising a gel forming component and the macromelecule to be crystallized, wherein at least one component of the trial is dispensed using an automatic liquid dispensing system.

28 Claims, 4 Drawing Sheets

OTHER PUBLICATIONS

Chayen et al, Acta Crystallographica, Section D, *New Developments of the IMPAX Small-Volume Automated Crystallization System*, vol. 50, (1994), pp. 456-458.

Blundell and Mizuguchi, Progress In Biophysics & Molecular Biology, *Structural Genomics: An Overview*, vol. 73, (2000), pp. 289-295.

Lorber and Giege, Journal of Crystal Growth, *Containerless Protein Crystallization in Floating Drops: Application to Crystal Growth Monitoring Under Reduced Nucleation Conditions*, vol. 168, (1996), pp. 204-215.

Mayans et al, Nature, *Structural Basis for Activation of the Titin Kinase Domain During Myofibrillogenesis*, vol. 395, Oct. 29, 1998, pp. 863-869.

Dennis Normile, SCIENCE, *Search for Better Crystals Explores Inner, Outer Space*, vol. 270, Dec. 22, 1995, pp. 1921-1922.

Sanchez et al, Nature Structural Biology, *Protein Structure Modeling for Structural Genomics*, vol. 7, Nov. 2000, pp. 986-990.

Saridakis and Chayen, Protein Science, *Improving Protein Crystal Quality by Decoupling Nucleation and Growth in Vapor Diffusion*, vol. 9, (2000), pp. 755-757.

Saridakis et al, ACTA Crystallographica Section D, *Phase Diagram and Dilution Experiments in the Crystallization of Carboxypeptidase $G_2$*, vol. 50, (1994), pp. 293-297.

Stevens, Structure, *Design of High-Throughput Methods of Protein Production for Structural Biology*, vol. 8, (2000), pp. R177-R185.

Stevens, Current Opinion in Structural Biology, *High-Throughput Protein Crystallization*, vol. 10, (2000), pp. 558-563.

Stock et al, SCIENCE, *Molecular Architecture of the Rotary Motor in ATP Synthase*, vol. 286, Nov. 26, 1999, pp. 1700-1705.

Russell et al, Structural Genomics Supplement to Nature Structural Biology, *Molecular Form & Function*, vol. 7, Nov. 2000, pp. 927-994.

Stura, In: Crystalliztion of Nucleic Acids and Proteins. (Ducruix, A. & Giege, R., eds.), *Seeding Techniques*, Oxford University Press, Oxford, pp. 177-208.

Yonath et al, Journal of Cellular Biochemistry, *Parameters for Crystal Growth of Ribosomal Subunits*, vol. 19, (1982), pp. 145-155.

Achilles, Contrib. Nephrol., *Crystallization in Gel Matrices: A New Experimental Model of Calcium Stone Formation*, vol. 58, (1987), pp. 59-64.

Achilles et at, Urol. Res., *An Optical Micromethod for the Determination of Relative Crystallisation Rates of Calcium Oxalate in Gels: Method and Preliminary Results*, vol. 11, (1983), pp. 87-91.

Brother et al, Z. Urol. U. Nephrol, *Gelmodell zur Messung von Kristallisations Inhibitoraktivitaten*, vol. 75, (1982), pp. 689-698 (In the Geman Language).

Chayen et al, Quarterly Reviews of Biophysics, *Trends and Challenges in Experimental Macromolecular Crystallography*, vol. 29, (1996), pp. 227-278.

D'Arcy et al, J. Crystal Growth, *A Novel Approach to Crystallising Proteins Under Oil*, vol. 168, (1996), pp. 175-180.

Drenth et al, ACTA Crystallographica Section D, *Nucleation in Protein Crystallization*, vol. 54, (1998), pp. 867-872.

McPherson et al, Structure, *Ways & Means*, vol. 3, (1995), pp. 759-768.

Blundell et al, Molecular Dimensions Limited—Jun. 2000 Newsletter.

Schneider et al, Urol. Int., *A Gel Model for Measuring Crystallization Inhibitor Activities*, vol. 38, (1983), pp. 33-38.

Dong et al, ACTA Crystallography, *Bound-Solvent Structures for Microgravity-Ground Control-, Gel-and Microbatch-Grown Hen Egg-White Lysozyme Crystals at 1.8 A Resolution*, 1999, D55, pp. 745-752.

Robert et al, Oxford University Press, *Crystallisation in Gels and Related Methods*, (1999).

Chayen, Protein Engineering, *A Novel Technique for Containerless Protein Crystallization*, 1996, vol. 9, No. 10, pp. 927-929.

Chayen, Structure, *The Role of Oil in Macromolecular Crystallization*, Oct. 15, 1997, vol. 5, pp. 1269-1274.

Chayen, ACTA Crystallography, *Comparative Studies of Protein Crystallization by Vapour-Diffusion and Microbatch Techniques*, 1998, D54, pp. 8-15.

Durbin and Feher, Annu Rev. Phys. Chem., *Protein Crystallization*, 1996, vol. 47, pp. 171-204.

Sawyer and Turner, Practical Approach, *X-Ray Analysis*.

METHODS OF CRYSTAL OPTIMIZATION

This application is a CON of PCT/GB02/01559 Apr. 2, 2002.

The present invention relates to techniques for optimising the crystallisation of macromolecules and their application to automated and high throughput systems.

The subject of crystallisation, especially protein crystallisation has gained a new strategic relevance in the next phase of the genome project in which X-ray crystallography will play a major role. There have been major advances in the automation of protein preparation and also in the X-ray analysis and bio-informatics stages once diffraction quality crystals are available. But these advances have not yet been matched by equally good methods for the crystallisation process itself. Automation is crucial for high throughput crystallisation as well as for the other phases of structural genomics since the search for good crystals requires the testing of many different crystallisation conditions. In the area of crystallisation, the main effort and resources are currently being invested into the automation of screening procedures to identify crystallisation conditions. However, in spite of the ability to generate numerous trials, so far only a small percentage of the proteins produced have led to structure determinations. This is because screening in itself is not usually enough; it has to be complemented by an equally important procedure in crystal production, namely crystal optimisation.

Figure 1:
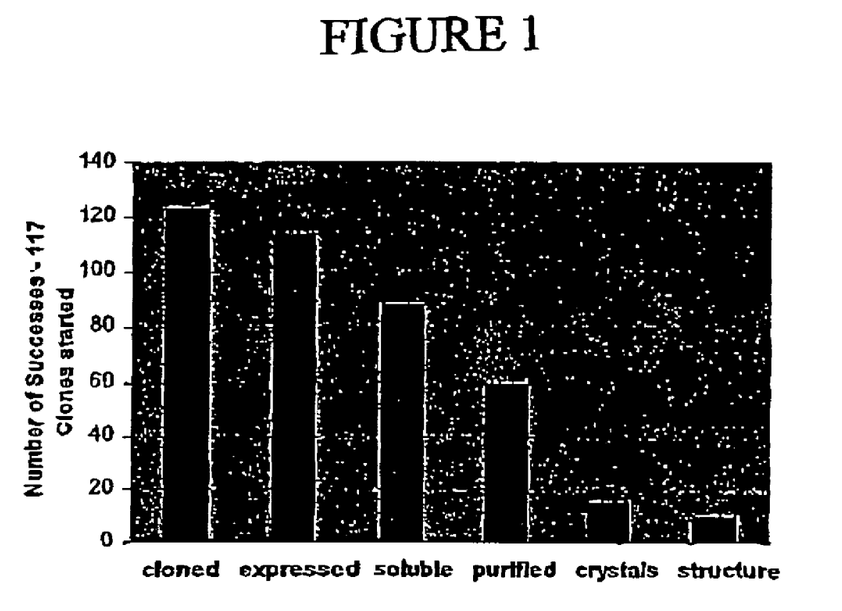
FIG. 1. The steps leading to X-ray structure determination and their success rates. Histogram showing the success rate of the different stages from clone to structure, taken from a progress report of a Structural Genomics project which is publicly available on the Internet (see text). Getting good crystals from purified protein is the main block to rapid progress.

The real stumbling block in structural genomics has become apparent from various pilot projects which are currently under way. These show that the success rate of getting from cloned protein to structure determination is only about 5–10%. For example, figures taken from the Human Protcome Structural Genomics pilot project [Brookhaven National Laboratory, The Rockefeller University and Albert Einstein College of Medicine: http://proteome.bnl.gov/progress.html] show that, out of 123 proteins which were cloned, 59 were purified. Of these 59, 33 yielded some crystals of some sort. However, only 15 of these crystals were of good enough quality to be useful for structure determination and only 10 have been solved to date (FIG. 1). Clearly this is highlighting a general problem where, even if protein can be cloned, expressed, solubilised and purified, and even if crystallisation trials do yield some crystals, this usually does not guarantee that the crystals will be good enough for the structure to be solved. For structural genomics to be productive, it is essential that this problem is addressed.

Recently major advances have been made both in the automation of protein expression and purification methods [1] and in X-ray analysis [2] and modelling [3]. In the case of crystallisation, now that commercial screening kits and computer algorithms for designing arrays of potential conditions are readily accessible, it is no longer a major problem to dispense trials automatically [4,5]. Automatic generation of high throughput screening crystallisation trials is also underway [2,6].

The first semi-high-throughput experiments for both screening and optimisation were designed in 1990 as microbatch trials under oil [4]. Microbatch trials consisting of 0.7–2 μl drops of a mixture of protein and crystallising agents are generated by an automated liquid dispensing system and are dispensed and incubated under oil in order to prevent evaporation. The automated liquid dispensing system may have two modes of action: one to automatically screen numerous potential crystallisation conditions and the other for optimisation of the most promising screening conditions using a matrix survey [9,10]. The microbatch method has established a unique way of crystallising macromolecules, and many target proteins have been successfully crystallised using it [e.g. 11,12,13]. In its current state, a single automated liquid dispensing system machine can generate about 2000 trials, per day. Because batch is mechanically the simplest crystallisation method, this procedure lends itself for adaptation to high-throughput crystallisation. The microbatch method has already been adapted for high throughput screening experiments in the USA using a large bank of syringes dispensing 0.4–0.5 μl volumes into 1536-well microassay plates [6].

However, there are a number of issues that still require attention. These so include: i) the large amount of manual preparation needed prior to automated dispensing, (ii) the issue of cleaning hundreds of syringes and (iii) the viewing, follow-up and analysis of the results. Some proteins will surely crystallise during this initial screening, but most trials are likely to yield microcrystals or low-ordered crystals. The conversion of such crystals into useful ones requires individualised optimisation techniques. Such techniques do not lend themselves readily to automation and they have yet to be adapted to cope with the huge volume of experiments required by genome projects. Consequently, the subject of optimisation has been rather neglected, apart from the obvious first step of merely changing the concentrations or pH around the conditions of interest. There is consequently a need for high-throughput automated optimisation methods which go beyond the usual fine-tuning of conditions at every stage in structural genomics.

Optimisation methods have been used in crystallising proteins that could not have been crystallised otherwise [e.g. 7,8].

We have now developed automated optimisation techniques suitable for high throughput trials.

A first aspect of the invention provides an automated method of optimising crystallisation conditions for a macromolecule comprising the step of forming a crystallisation trial, the trial comprising a sample comprising (i) a gelforming component and (ii) the macromolecule to be crystallised, wherein at least one component of the trial is dispensed using an automatic liquid dispensing system.

The macromolecule may be any macromolecule, but it is preferably a biological macromolecule. Preferably, it is, or comprises, a polypeptide or polynucleotide, as discussed further below.

By "trial" we include a series of two or more test conditions, which conditions vary according to factor such as the nature and/or concentration of crystallisation agents, the concentration of the macromolecule to be crystallised, the concentration or type or state of the gel forming component, the temperature, time of incubation and so on. A trial of the invention includes a screen comprising more than one sample, which screen is designed to determine the optimal conditions for crystallisation of a macromolecule. By "optimal conditions" we mean those conditions which produce or promote or induce the production or growth of crystals of the macromolecule in such a form that they are more suitable for x-ray analysis, or allow generation of useful or higher resolution structural data by x-ray analysis. Crystals which are suitable for x-ray analysis are known to have a minimal requirement for size, quality and form.

Preferably, the gel-forming component in the sample is or comprises agarose or tetramethyl ortho silane (TMOS). TMOS is especially preferred particularly when used at a final concentration of 0.2%. Methods of preparing gel solutions are well known in the art, and are described in detail in Robert et al in the book *Crystallography* (Chapter 6 p149–175) from the "Practical Approach" series: Crystallization of nucleic acids and proteins: a practical approach, $2^{nd}$ ed. 1999 (eds. Ducruix, A. & Giegé, R.) Oxford University Press, Oxford, and in Example 1.

Previous manual methods of crystallising macromolecules, for example proteins which used gel as a crystallisation max required relatively large amounts of the gel/crystallisation mixture (more than 10 μl) and were not automated. An advantage of the present method is the requirement for only small volumes of gel/crystallisation mixture. Hence, preferably the total volume of the gel/crystallisation mixture dispensed is less than 5 μl, and more preferably between 1.5 μl and 2 μl. The volume may be even lower: for example, we have generated gelled drops of 0.3 μl volume.

Use of a gel matrix has not previously been automated because a suitable automatic means of dispensing the gel matrix did not appear to be available. Surprisingly, we have found that dispensing the gel using an automated liquid dispensing system as is already available does not result in clogging of the fine dispensing tip, and such a dispensing system may be used with a range of gel matrices.

According to a preferred embodiment of this aspect of the invention, the trial further comprises oil such that the oil is a layer over the sample and the oil layer may permit diffusion/evaporation from the sample. Typically, in these embodiments the sample is in microbatch. A containerless system may be used, in which the sample sits between layers of oil of different density, one of greater density than the sample and one of lower density than the sample.

Conveniently in this embodiment, the gel-forming component is dispensed into wells of a multi-well assay plate, such as a 1536-well microassay plate.

It will be appreciated that the gel-forming component on such a plate may have been dispensed and have gelled some time before the oil is added, or may be dispensed after the oil has been dispensed. It will further be appreciated that the oil may be added after the gel-forming component has been applied to the surface, but prior to application of the liquid comprising the macromolecule.

Preferably, the oil is dispensed first, and the gel forming component and macromolecule are administered subsequently, either together in a single step, or separately or sequentially in any order. Suitable oils are described in more detail below.

According to a preferred form of this embodiment, the sample is placed onto a hydrophobic surface, preferably one which is hydrophobic due to a layer of grease. The grease may be any grease which acts as a hydrophobic barrier between the support and the gel/macromolecule sample and which is not reactive with the sample. Suitable greases may have a low melting point to allow melting the grease for even application onto the surface. Preferably the grease is a high-vacuum silicone grease. The advantage of the hydrophobic surface is the reduction of contact with the support surface in microbatch, without the need for suspending the sample between two oils of different densities. This thereby facilitates subsequent collection of the sample.

According to an alternative preferred embodiment of the first aspect of the invention, the crystallisation method may utilise the hanging drop technique. Thus, the method of the first aspect of the invention may further comprise the steps of (i) incubating the sample as a drop in the presence of a first reservoir with a composition having a higher solute concentration that that of the sample; and (ii) transferring the drop into the presence of a second reservoir with a composition having a lower solute concentration than the first reservoir by means of an automatic robot.

Crystal nucleation requires different conditions to those of crystal growth. The drop of sample containing the macromolecule and the crystallisation agents is at a concentration of macromolecule and crystallisation agents which is lower than that required for the formation of crystals. This drop is equilibrated against a reservoir of higher concentration of crystallisation agents, which has the effect of concentrating the macromolecule in the drop until equilibrium is reached. Such conditions are suitable for promoting nucleation. It is desirable to halt nucleation in order to obtain a smaller number of crystals which are larger and more regular. In order to halt nucleation and instead promote crystal growth, the conditions surrounding the gelled sample drop are switched to a lower solute concentration so that removal of the solvent from the sample drop is slowed or stopped, or may even be reversed.

Hence, it is preferred that the length of incubation of step (i) is sufficient to allow nucleation of a small number of crystals, but is no longer than that. At the end of this nucleation incubation, the sample drop is transferred to the low solute concentration conditions and incubated in these conditions to permit crystal growth. Determination of the length of time required for equilibration using liquid samples is well known in the art, and determination of a suitable incubation time for equilibration where the sample is gelled can be done using only routine experimentation.

As described by Chayen (1997) *Structure* 5:1269–1274, oil can be layered over the reservoir containing the high solute concentration conditions of step (i) to slow down the equilibration rate of the trial as supersaturation is approached. Suitable oils are described in more detail below.

For automation of this embodiment, the transfer of samples between the conditions of step (i) and step (ii) may be done using robot. Suitable robots are known in the art of vapour diffusion crystallography, and an example is the Cyberlab C200 robot produced by Cyberlab, Inc, a subsidiary of Gilson, Inc. (UK distributors are Anachem Ltd, Anachem House, Luton, Beds. UK)

According to the invention, at least one component of the trial in the method of the fist aspect is dispensed using an automated liquid dispensing system. Preferably this component is the gel forming component. Preferably, at least two components (eg the gel forming component and the macromolecule to be crystallised or any oil) are dispensed using the said system. Where the gel-forming component and the macromolecule to be crystallised are two or more separate liquids, it is preferred if both or all of the liquids are dispense using an automated system. More than one liquid may be dispensed from the same tip of the automated liquid dispensing system. Preferably, where oil and the sample or sample components are both dispensed automatically, the oil and the sample components are dispensed from at least two separate tips of the system It will be appreciated that the sample comprising the gel-forming component and macromolecule may be formed by two sequential steps wherein the gel-forming component is applied to a surface and the macromolecule is subsequently added to the gel-forming component. The gel-forming component may be dispensed as a solution or suspension or any other convenient liquid form. The liquid gel-forming component may have set prior to addition of a liquid comprising the macromolecule or may it still be liquid at that stage. The resulting composition of gel-forming component and macromolecule is included within the scope of term "sample" in the first aspect of the present invention.

Where the sample is under an oil layer (for example, in microbatch methods), or where a layer of oil is used over a reservoir (for example, in vapour diffusion/hanging drop crystallisation), the oil layer may constitute a single type of oil, or may be a mixture of oils. Use of a mixture of oils over a crystallisation sample is described in D'Arcy et al. (1996) *J. Crystal Growth* 168, 175–180, and is a way of altering the rate of diffusion trough the oil layer, since oils vary in their permeability properties. Where the oil layer includes more than one type of oil, it may include silicone, which permits more diffusion than, for example, paraffin does. Preferably, the mixture of oils includes a suitable low density oil such as paraffin with a density of 0.84 g cm$^{-3}$. A suitable paraffin is commercially available from Hampton Research, California 92677-3913 USA under catalogue number HR3-411. Where the oil layer comprises only a single type of oil, it is prefixed if the oil is paraffin. It is important that the density of the oil is less than that of the sample or the reservoir creating high or low concentration conditions, since the layer of oil should rest over the sample or reservoir. Hence, where the oil is a layer over the sample, the dispensed drop of sample should sink beneath the oil surface, or where the oil is added after the sample, the oil should remain on top of the sample and not sink below it. In this way the oil can act as a (potentially vapour permeable) sealant of the conditions within the sample.

It will be appreciated that the thickness of the oil (either as a layer over the sample in a microbatch type method, or as a layer over the first reservoir where a hanging drop is suspended over a first reservoir of a composition with a higher solute content than the crystallisation sample), and the nature of the oil are important in determining the environment of the sample. For example, a minimum thickness of oil may be required in order to prevent evaporation of solvent from the sample. However, it may be desirable to allow a degree of evaporation from the sample, for example because the macromolecule concentration in the sample is undersaturated, and a gradual evaporation of solvent is required to increase the macromolecular concentration to a level where crystallisation may occur. Evaporation from the sample may be allowed by using a thinner layer of oil, for example, less than 3.5 mm trick. Alternatively, evaporation may be permitted by using an oil or oil mixture which permits evaporation. The speed of evaporation may be controlled by varying the thickness or ratio of oil components of the layer. The effect of such oil mixtures and thicknesses is known in the art of protein crystallography and are described in Chayen (1997) *J. Appl. Cryst.* 30:198–202.

Preferably, the oil layer permits diffusion between the environment and the sample containing the macromolecule and the crystallisation agents due to the thinness of the layer. It has been observed that the diffusion through a thick layer of paraffin is negligible. However, when the thickness of the layer is reduced, diffusion may occur. The extent of diffusion may be proportional to the thickness of the paraffin layer, and choosing an appropriate thickness of oil may allow the desired rate of evaporation to be determined. Typically, the thickness of the layer of oil at which evaporation ceases to be negligible is 3.5 mm. Preferably, the thickness of the layer is between 0.7 to 1.2 mm.

Preferably, the rate of diffusion is detectable and is not negligible. By "negligible" we mean the evaporation is undetectable over a period of at least a day, preferably over a period of at least 2 days, or 5 days or a week. Preferably, negligible evaporation is a loss of water from a sample which is sufficiently small that it cannot be detected after a period of at least two weeks or 1 month or 2 months or 3 months. Evaporation or diffusion from the sample drop may be judged by any suitable means, including by assessment of the size of the sample drop, or by the appearance of dryness.

Hence, preferably the concentration of the dispensed macromolecule solution invention is supersaturated, but it may be undersaturated or metastable. In other words, the concentration of the sample may be outside the nucleation zone of the phase diagram of that sample, and may reach the nucleation zone by evaporation of solvent from the sample.

The macromolecule may be any macromolecule. Preferably it is a biological macromolecule such as nucleic acids, complex polysaccharides and viruses. Preferably, the biological macromolecules are polypeptides. A polypeptide comprises at least one chain of amino acid residues which are covalently joined by peptides bonds. A polypeptide chain may have any number of amino acid residues, preferably at least two, more preferably at least 100, 500, 1000 or 2000. The polypeptide chain may have more than 2000 residues. A polypeptide may contain residues in the chain which are unusual or artificial, and may comprise non-peptide bonds such as disulphide bonds. The residues may be further modified, for example to include a phosphate group or a sugar chain (eg an oligosaccharide) or a lipid moiety. A polypeptide may comprise more than one chain (for example, two chains linked by a disulphide bond between the sulphur in the side chain of cysteine residues), and may further comprise inorganic or organic co-factors or groups. Such modifications and additions are included within the term "polypeptide".

A second aspect of the invention provides a use of an automated liquid dispensing system capable of dispensing volumes of liquid between 0.1 μl to 5 μl for dispensing a gel-forming component and a sample comprising a macromolecule to be crystallised.

Automated liquid dispensing systems are known in the art of protein crystallography, and examples of a suitable system are the IMPAX and Oryx 6 machines produced by Douglas Instruments, Hungerford, Berks, UK. Preferably the liquid dispensing system is computerised to allow the machine to be programmed to dispense varying amounts and concentrations.

Preferably the gel-forming component used in the dispensing system is agarose or TMOS.

It will be appreciated that the gel-forming component dispensed by the system is fluid and not set whilst it is being dispensed. Gels which are useful in the present invention may form suspensions. Such gel suspensions tend to set within a few hours for a 5% TMOS gel, and overnight for a 0.2% TMOS gel.

A third aspect of the invention provides a use of a gel-forming component in automated optimisation of crystallisation of macromolecules.

Preferably the optimisation includes a method according to the first aspect of the invention.

It is further preferred if the macromolecules are biological macromolecules.

It is still more preferred if the macromolecules are polypeptides.

The gel forming component required by the second or third aspects of the invention may be any suitable gel-forming component. Preferably the final gel is 0.2% TMOS.

A fourth aspect of the invention provides a use of oil in a method according to the first aspect of the invention.

The oil may consist of one type of oil, or may be a mixture of oils. Where the oil is a mixture of oils, it is preferred that the mixture comprises silicone.

Preferably the oil of this aspect of the invention includes paraffin, regardless of whether the oil is a mixture of oils or a single type.

A fifth aspect of the invention provides a use of a grease in a method according to the first aspect of the invention.

Preferably, the grease is a high-vacuum silicon grease, and more preferably the grease is provided on a surface such as a multi-well assay plate.

A sixth aspect of the invention provides a use of an automated liquid dispensing system in a method according to the first aspect of the invention.

Preferably, the automated liquid dispensing system has at least two dispensing tips. Such automated systems are known in the art of protein crystallography, and an example is the IMPAX system made by Douglas Instruments, Hungerford, Berks, UK. It is further preferred if the automated liquid dispensing system is computerised, as described above.

A seventh aspect of the invention provides a kit of parts comprising an automated liquid dispensing system and a gel-forming component.

Preferably, the gel forming component is or comprises TMOS. Preferably the dispensing system is one as described above.

In a preferred embodiment of this aspect of the invention, the kit further comprises a low density oil such as paraffin or silicone oil.

An eighth aspect of the invention provides a kit of parts comprising an automated liquid dispensing system, low density oil and grease.

Preferably, the grease is a high-vacuum silicon grease, and more preferably, the grease is provided on a suitable surface such as on a multi-well plate.

According to a preferred embodiment of this aspect of the invention, the kit oil provided with the kit is paraffin.

The invention will now be described in more detail with the aid of the following Figures and Examples.

EXAMPLE 1

Development of Optimisation Procedures

Crystallisation in Gels

Growth of crystals in a gel medium can improve the quality of crystals in comparison with solution media because convection and sedimentation are reduced [14]. The application of gels in the crystallisation of macromolecules, particularly proteins, has been pursued for more than 10 years, yet the method remains relatively underused. This may be due to the relatively complicated procedures required when applying gels to cystallisation trials and also to the relatively large quantities (mostly >10 μl) of sample needed.

Very recently a simple automatic way to generate gelled crystallisation trials by harnessing the IMPAX automated crystallisation system has been developed IMPAX works as a 5-channel system where precipitant, buffer, protein etc. are put into different channels and dispensed through a fine tip by the action of motorised syringes. By placing a gel solution in one of the channels it is possible to automatically dispense microbatch trials which form the gel/crystallisation mixtures in final volumes of 1.5–2 μl. This can be achieved with the same ease as conventional automated microbatch trials. The gel solution is loaded into the liquid handling apparatus in the same way as the other ingredients of the crystallisation trial. Then, while still a low viscosity liquid, it is dispensed under oil simutaneously with all the other ingredients. After a known time, which should ideally be before the start of the nucleation process, polymerisation occurs and the drop gels. Agarose gels and silica gels, one made by neutralisation of sodium metasilicate and another by hydrolysis of tetramethyl ortho silane (TMOS), have been tested with trypsin, thaumatin, concanavalin A, lysozyme, and a cyanin protein.

Figure 2:
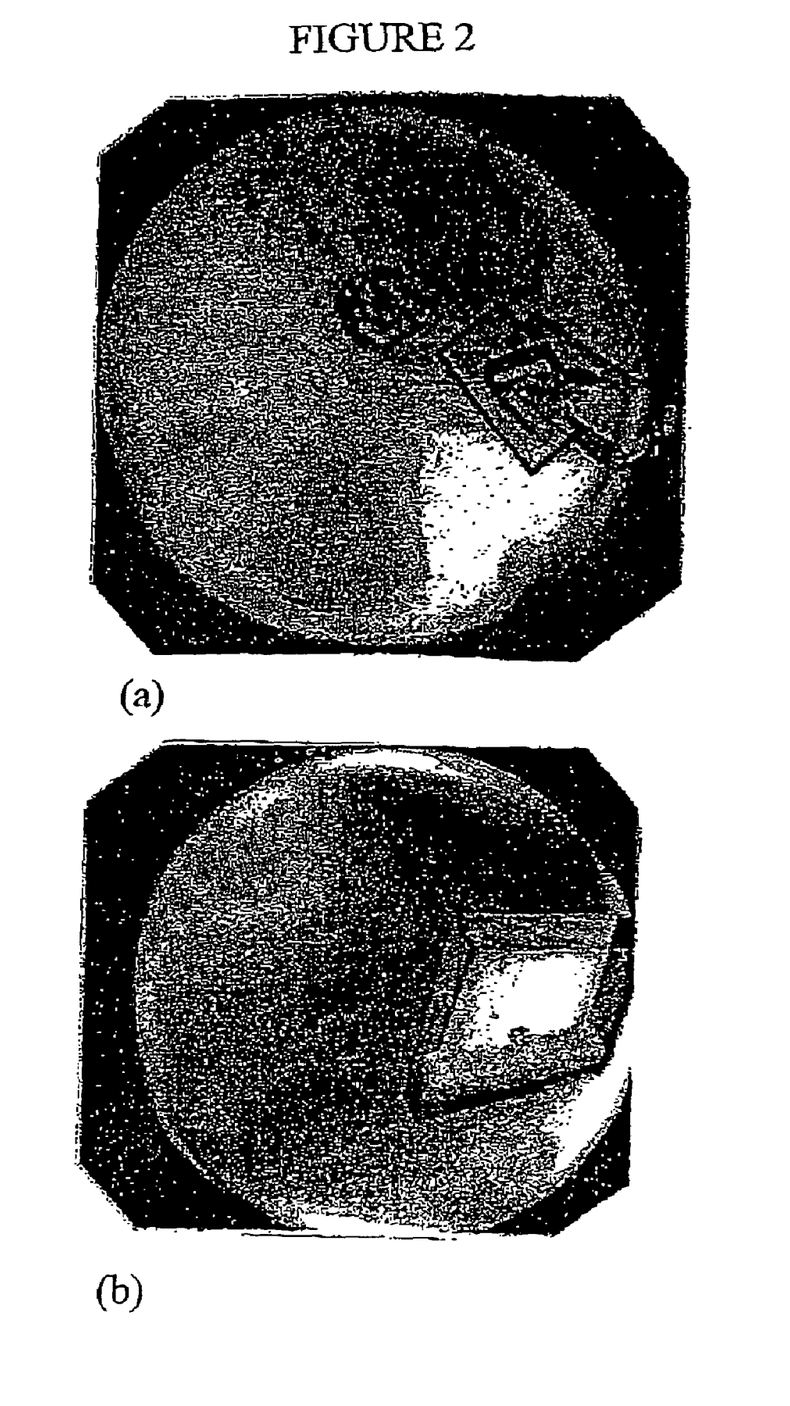
FIG. 2. Standard and gelled drops in microbatch.
(a) Trypsin crystals grown in a standard 2 μl microbatch drop. Size of largest crystal 300×180×80 μm.
(b) Trypsin crystal grown in a 2 μl gelled (TMOS) microbatch drop under otherwise the same conditions as (a). The crystal measurements are 320×300×120 μm.
Both photographs were taken at the same magnification.

In most cases, a higher proportion of the total crystal yield consisted of large, usable crystals in the gelled drops (FIG. 2) compared with smaller crystals in microbatch trials in conventional solutions. In order to test whether the gels would make a difference even under sub-optimal (e.g. initial screening) conditions, concanavalin A was crystallised in the presence of either agarose or TMOS gels in conditions which normally gave many small crystals. The presence of TMOS gel still made a striking difference; fewer, larger crystals were obtained. TMOS at a concentration of 0.2% has consistently given the best results with all five proteins used in the initial tests.

Materials and Methods

Preparation of the TMOS Gel

For making 2 ml 5%(v/v) gel:

Place 1 ml of distilled water in a glass or Eppendorf™ tube. Add 0.1 ml TMOS solution (Fluka catalogue no. 37682) and shake well to disperse. Make up to 2 ml and continue shaking for 10–15', preferably keeping the vessel covered, eg. with Parafilm™. The resulting solution will gel within a few hours. Unlike with agarose gel which does need heating, with TMOS gel there is no need to heat the solution.

A 5% TMOS gel solution will gel in a few hours, but the 0.2% TMOS gel (which is the preferred gel concentration in the crystallisation drop) takes overnight to gel.

Example of Gel Conditions for Crystallising the Protein Thaumatin 19.6 mg/ml thaumatin (dispensed from a 50 mg/m stock)
6.5% sodium potassium tartrate
50 mM PIPES buffer, pH 6.8
0.2%(v/v) TMOS gel (from a 5% initial stock)

The liquid drops were dispensed by the IMPAX robot.

At room temperature (ca. 20° C.), an average of 20 small crystals and microcrystals were formed in the standard (non-gelled) controls. In the gelled drops, 4–10 large crystals were formed.

EXAMPLE 2

Containerless Crystallisation

Heterogeneous nucleation, which is often detrimental to the production of diffraction quality crystals, can be induced by the contact of a crystallisation trial with the walls of its supporting vessel [15,16]. Crystallisation in a 'containerless' set up, in which a crystallisation drop is suspended between two oils of different densities, results in reduction of heterogeneous nucleation [17,18,19] thus leading to the production of a smaller number of high quality crystals. This two-oil method was useful for manually setting up a small number of experiments, but it took time to layer the oils, it was difficult to harvest the drops and the method was not amenable to automation.

Figure 3:
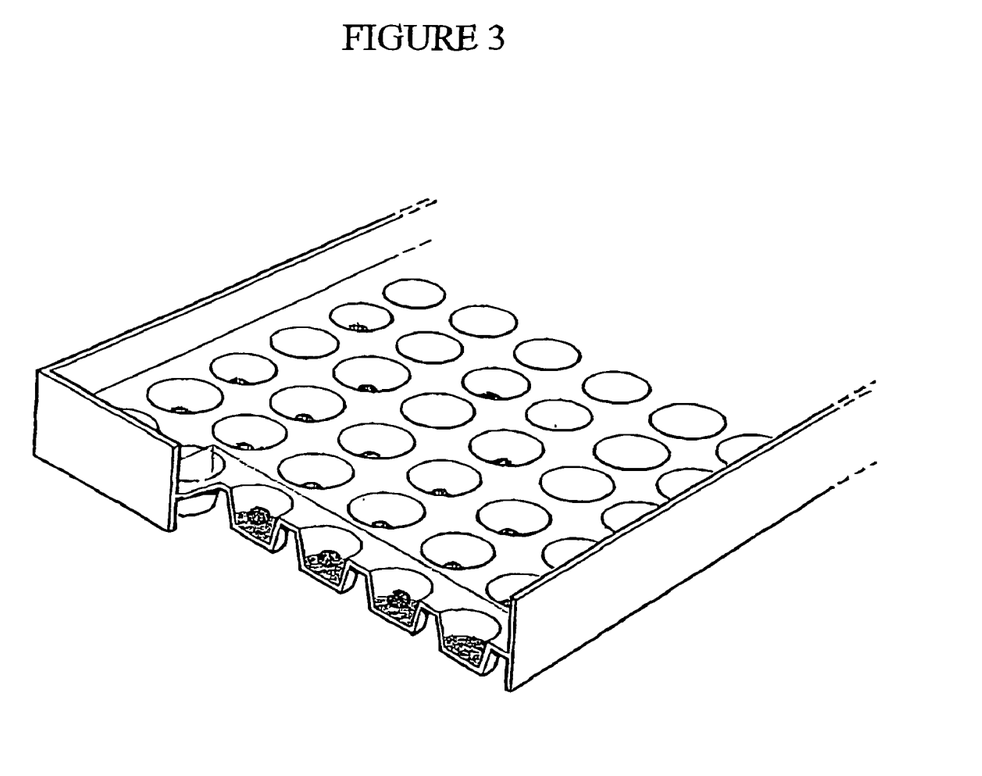
FIG. 3. Containerless crystallisation setup. Schematic diagram of crystallisation drops positioned between silicon grease (on the surface of the plate in grey) and low-density oil (laid on top) inside a microbatch plate.

High-throughput can now be achieved by a modification of the original containerless method. The lower layer, previously consisting of a heavy fluorosilicone oil, is replaced with a hydrophobic surface of high-vacuum silicone grease. The grease covers the bottom of the crystallisation plate onto which the trial drops are automatically dispensed using the automated liquid dispensing robot (FIG. 3). A low-density oil, usually paraffin oil (density 0.84 g/cm$^3$), is applied as the top layer. The greased surface has an added advantage over the original two-oil set up in that the grease provides a stable interface to the upper layer. This prevents crystals from migrating to the walls, thus making them much easier to harvest. The crystals can be lifted out with a loop or even a spatula. Moreover, vacuum grease is much cheaper as a lower layer than is fluorosilicone oil.

Application of Grease

In a preferred method, the grease is melted and poured onto the plate covering the bottom of the wells in the plate. Within a given time it solidifies (the time required for solidification will depend on the grease used).

Optimisation by Decoupling Nucleation and Growth

Figure 4:
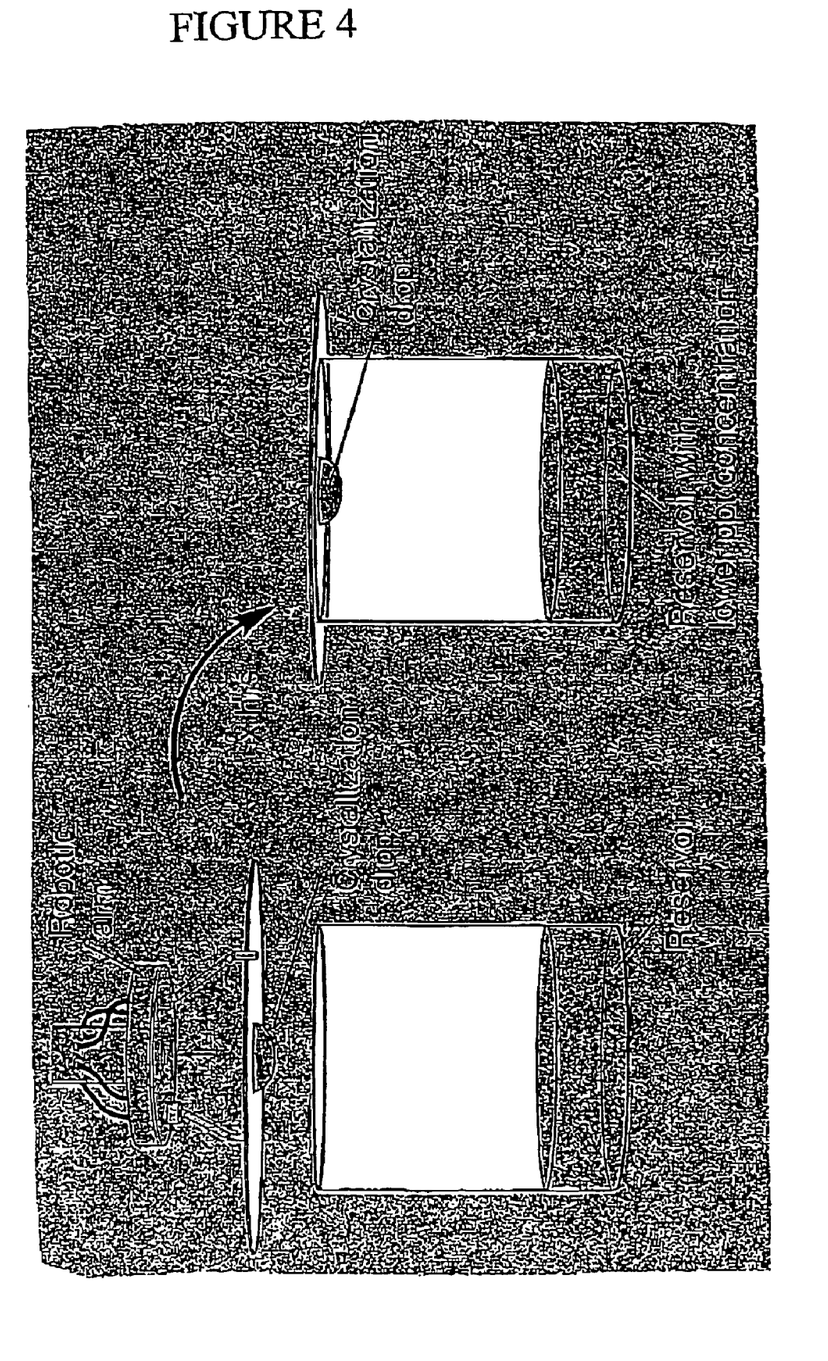
FIG. 4. Automatic transfer of hanging drops from nucleation to growth conditions.

Nucleation requires different conditions to those of growth. The most common way of de-coupling nucleation and growth is by seeding [20]. However, quenching of nucleation using dilution is more amenable to high throughput processing. Dilution can be achieved in both microbatch [21] and hanging drop methods [22]. In the case of hanging drops, the coverslips holding the drops are incubated for some time over solutions that normally give many small crystals. After a given time they are then transferred to reservoirs with lower solution concentrations that normally yield clear drops. In the case of microbatch the drops are diluted by automated means after incubation. We have so far reported successful use of these techniques only in highly individualised experiments where nucleation and metastable conditions, as well as optimal timing; had been painstakingly fine-tuned to the system in band [21,22, M. Kokkinidis, personal communication]. We have now tested the suitability of this approach for high-throughput optimisation. Vapour diffusion drops were transferred at random times from a standardised set of high-concentration conditions to a lower concentration reservoir. Preliminary results indicate that the average number of trials leading to good crystals is higher when using this method, compared with using a screen consisting of only either the high or the low concentration sets of conditions. In the case of hanging drops, this transfer between conditions can be done automatically with robots such as the Cyberlab (FIG. 4).

REFERENCES

1. Stevens, R. C. (2000). Design of high-throughput methods of protein production for structural biology. *Structure* 8, R177–R185.
2. Abola, E., Kuhn, P., Earnest, T. & Stevens, R. C. (2000). Automation of X-ray crystallography. *Nature Struct. Biol.* 7, 973–977.
3. Sánchez, R., Pieper, U., Melo, F., Eswar, N., Martí-Renom, M. A., Madhusudhan, M. S., Mirkovic, N. & Sali, A. (2000). Protein structure modelling for structural genomics. *Nature Struct. Biol.* 7, 986–990.
4. Chayen, N. E., Shaw Stewart, P. D., Maeder, D. L. & Blow, D. M. (1990). An automated system for microbatch protein crystallisation and screening. *J. Appl. Cryst.* 23, 297–302
5. Stevens, R. C. (2000). High-throughput protein crystallization *Curr. Opin. Struct Biol.* 10, 558–563.
6. Luft, J. R., Wolfley, J., Bianca, M., Weeks, D., Jurisica, I., Rogers, P., Glasgow, J., Fortier, S. & DeTitta, G. T. (2000). Gearing up for ~40K crystallization experiments a day: meeting the needs of HTP structural proteomics projects. *The 8$^{th}$ International Conference on the Crystallization of Biological Macromolecules Oral Presentation Abstracts*, p.29.
7. Mayans, O., van der Ven, P. F. M., Wilm, M., Mues, A., Young, P., Fuerst, D., Wilmanns, M. & Gautel, M. (1998). Structural basis for activation of the titin kinase domain during myofibrillogenesis. *Nature* 395, 563–869.
8. Normile, D. (1995). Search for better crystals explores inner, outer space. *Science* 270, 1921–1922.
9. Chayen, N. E., Shaw Stewart, P. D. & Blow, D. M. (1992). Microbatch crystallisation under oil—a new technique allowing many small-volume crystallisation trials. *J. Cryst. Growth* 122, 176–180.
10. Chayen, N. E., Shaw Stewart, P. D. and Baldock, P. (1994). New developments of the IMPAX small-volume crystallisation system. *Acta Cryst.* D50, 456–458.
11. Stock, D., Leslie, A. G. W. & Walker, J. E. (1999). Molecular architecture of the rotary motor in ATP synthase. *Science* 286, 1700–1705.
12. Barrett, T. E., Savva, R., Panayotou, G., Barlow, T., Brown, T., Jiricny, J. & Pearl, L. H. (1998). Crystal structure of a G:T/U mismatch-specific DNA glycosylase: mismatch recognition by complementary-strand interaction. *Cell* 92, 117–119.
13. Chayen, N. E. (1998). Comparative studies of protein crystallisation by vapour diffusion and microbatch. *Acta Cryst.* D54, 8–15.
14. Robert, M.-C., Vidal, O., Garcia-Ruiz, J.-M. & Otálora, F. (1999). Crystallization in gels and related methods. In *Crystallization of Nucleic Acids and Proteins*. (Ducruix, A. & Giegé, R., eds.), pp.149–175, Oxford University Press, Oxford.
15. Yonath, A., Mussig, J. & Wittman, H. G. (1982). Parameters for crystal growth of ribosomal subunits. *J. Cell Biochem.* 19, 145–155.
16. Blow, D. M., Chayen, N. E., Lloyd, L. F. & Saridakis, E. (1994). Control of nucleation of protein crystals. *Protein Sci.* 3, 1638–1643.
17. Chayen, N. E. (1996) A novel technique for containerless protein crystallisation. *Protein Engineering* 9, 927–929.
18. Lorber, B. & Giegé, R. (1996). Containerless protein crystallization in floating drops: application to crystal growth monitoring under reduced nucleation conditions. *J. Cryst. Growth* 168, 204–215

19. Chayen, N. E. (1997). The role of oil in macromolecular crystallisation. *Structure* 5, 1269–1274.
20. Stura, E. A. (1999). Seeding techniques. In *Crystallization of Nucleic Acids and Proteins*. (Ducruix, A. & Giegé, R., eds.), pp.177–208, Oxford University Press, Oxford.
21. Saridakis, E. E. G., Shaw Stewart, P. D., Lloyd, L. F. & Blow, D. M. (1994). Phase diagram and dilution experiments in the crystallization of carboxypeptidase $G_2$. *Acta Cryst.* D50, 293–297.
22. Saridakis, E. & Chayen, N. E. (2000). Improving protein crystal quality by de-coupling nucleation and growth in vapour diffsion". *Protein Sci.* 9, 755–757.
23. Chayen, N. E. (1997). A novel technique to control the rate of vapour diffusion, giving larger protein Crystals. *J. Appl. Cryst.* 30, 198–202.
24. Abbott, A. (2000). Structures by numbers (news feature). *Nature* 408, 130–132
25. Structural Genomics supplement to *Nature Struct. Biol.* 7, 927–994.

Focussed issue: Structural Genomics. *Prog. Biophys. Mol. Biol.* 73, 289–36.

The invention claimed is:

1. An automated method of optimising crystallisation conditions for macromolecules comprising forming a crystallisation trial, the trial comprising a sample comprising:
   (a) a gel forming component; and
   (b) a macromolecule to be crystallised, wherein at least one component of the trial is dispensed using an automatic liquid dispensing system.

2. A method according to claim 1 wherein a layer of oil is present over the sample.

3. A method according to claim 2 wherein the sample and oil are dispensed from different tips of the automatic liquid dispensing system.

4. A method according to either one of claims 2 or 3 wherein the oil is dispensed first and the sample is dispensed under the oil.

5. A method according to claim 1 or claim 2 or claim 3 wherein a surface onto which the gel-forming component or sample is dispensed is a greased surface.

6. A method according to claim 5 wherein the grease is a high-vacuum silicone grease.

7. A method according to claim 1 further comprising:
   (c) incubating the sample as a drop in the presence of a first reservoir with a composition having a higher solute concentration that that of the sample; and
   (d) transferring the drop into the presence of a second reservoir with a composition having a lower solute concentration than the first reservoir by means of an automatic robot.

8. The method according to claim 7 wherein the first reservoir composition is covered with a layer of oil.

9. A method according to either one of claims 2 or 8 wherein the oil layer permits diffusion from the sample.

10. The method of either one of claims 2 or 8 wherein the oil layer includes paraffin.

11. The method of claim 10 wherein the oil layer consists of paraffin.

12. The method of either one of claims 2 or 8 wherein the oil layer is a mixture of oils.

13. The method of claim 12 wherein the oil layer comprises silicone.

14. The method according to either one of claims 1 or 7 wherein the gel-forming component is or comprises a material selected from the group consisting of agarose and tetramethyl ortho silane (TMOS).

15. The method of claim 14 wherein the gel-forming component is or comprises tetramethyl ortho silane (TMOS) and is at a final concentration of 0.2%.

16. The method of either one of claims 1 or 7 wherein the volume of sample dispensed is less than 5µl.

17. The method of claim 16 wherein the volume of sample is between 1.5µl and 2µl.

18. The method of either one of claims 1 or 7 wherein the sample is dispensed into wells of a 1536-well microassay plate.

19. A method according to either one of claims 2 or 8 wherein the oil layer over the sample permits vapour diffusion between the sample and the environment due to the thinness of the layer.

20. A method according to either one of claims 1 or 7 wherein the macromolecule is a biological macromolecule.

21. A method according to claim 20 wherein the biological macromolecule is a polypeptide.

22. A method according to either one of claims 1 or 7 including the use of a material selected from the group consisting of one or more oils.

23. A method according to claim 22 wherein the oil includes a material selected from the group consisting of silicone, paraffin and grease including high-vacuum silicone grease.

24. A method according to claim 23 wherein the grease is provided on a multi-well plate.

25. A method according to either one of claims 1 or 7 further comprising using an automated liquid dispensing system capable of dispensing volumes of liquid between 0.1µl to 5µl for dispensing a sample of gel-forming component and a macromolecule to be crystallized.

26. An automated method of optimizing crystallization conditions for macromolecules comprising using an automated liquid dispensing system capable of dispensing volumes of liquid between 0.1µl to 5µl for dispensing a sample of gel-forming component and a macromolecule to be crystallized.

27. A method according to claim 26 wherein the gel-forming component is 0.2% tetramethyl ortho silane (TMOS).

28. A method according to claim 26 wherein the automated liquid dispensing system is selected from machines computerized and programmed to dispense varying amounts and concentrations of material.

* * * * *